US006755044B1

(12) United States Patent
    Hildebrandt

(10) Patent No.: US 6,755,044 B1
(45) Date of Patent: Jun. 29, 2004

(54) HEATER-EVAPORATOR

(75) Inventor: Marc J. Hildebrandt, Midland, MI (US)

(73) Assignee: King Refrigeration, Inc., Freeland, MI (US)

(*) Notice: Subject to any disclaimer, the term of this patent is extended or adjusted under 35 U.S.C. 154(b) by 0 days.

(21) Appl. No.: 10/356,700

(22) Filed: Jan. 31, 2003

Related U.S. Application Data

(60) Provisional application No. 60/353,337, filed on Feb. 1, 2002.

(51) Int. Cl.⁷ .................. F25D 21/06; F25D 21/00; H05B 3/06
(52) U.S. Cl. .................. 62/276; 62/234; 62/275; 219/523; 219/531
(58) Field of Search .................. 62/276, 234, 275; 70/60.11, 61.46; 219/523, 531

(56) References Cited

U.S. PATENT DOCUMENTS

| 2,907,861 | A | * | 10/1959 | Melton ................ 219/521 |
| 3,350,922 | A | | 11/1967 | Kim et al. |
| 4,621,182 | A | * | 11/1986 | Driggers ................ 219/85.13 |
| 5,503,002 | A | | 4/1996 | Selby et al. |
| 5,824,886 | A | * | 10/1998 | Selby et al. ............... 73/60.11 |
| 5,852,230 | A | | 12/1998 | Selby et al. |
| 6,009,748 | A | | 1/2000 | Hildebrandt et al. |

OTHER PUBLICATIONS

Hildebrandt et al., U.S. patent application Ser. No. 10/077,236 filed Feb. 15, 2002 A.D.
Hildebrandt, U.S. patent application Ser. No. 60/353,337 filed Feb. 1, 2002 A.D.
Hildebrandt et al., U.S. patent application Ser. No. 60/354,994 filed Feb. 8, 2002 A.D.

* cited by examiner

*Primary Examiner*—William C. Doerrler
*Assistant Examiner*—Filip Zec
(74) *Attorney, Agent, or Firm*—Christopher John Rudy

(57) ABSTRACT

Heater-evaporator has a hollow refrigerator fluid evaporator body with which is incorporated a heater. The body can enclose the heater, which is separate from the body, or the body and the heater can be part of one another. The heater can be heated by any suitable means, to include electrical resistance and/or induction. The invention can be utilized in refrigeration and temperature control, to include, for example, in laboratory test devices requiring refrigeration and temperature control.

20 Claims, 7 Drawing Sheets

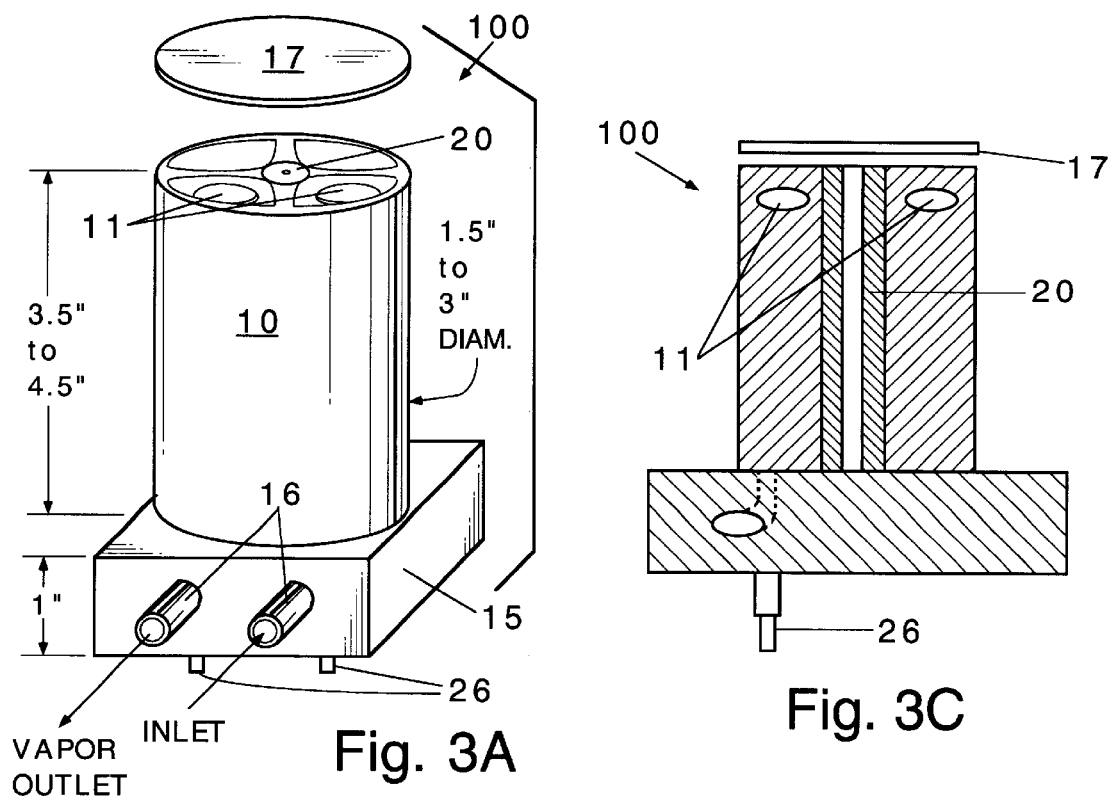
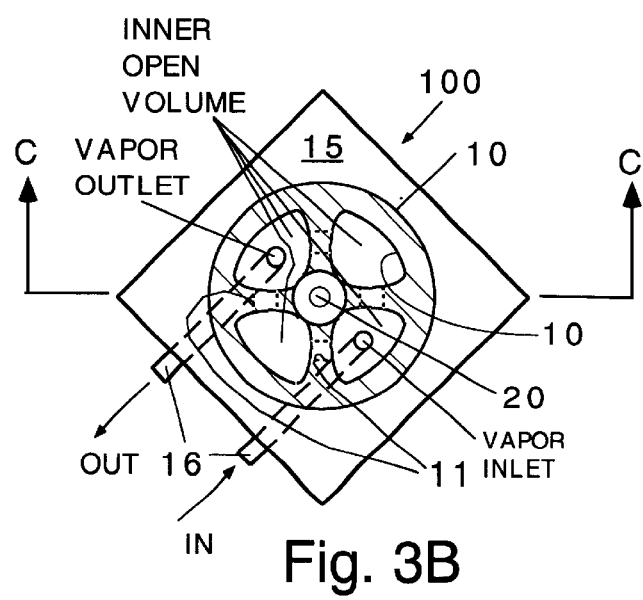

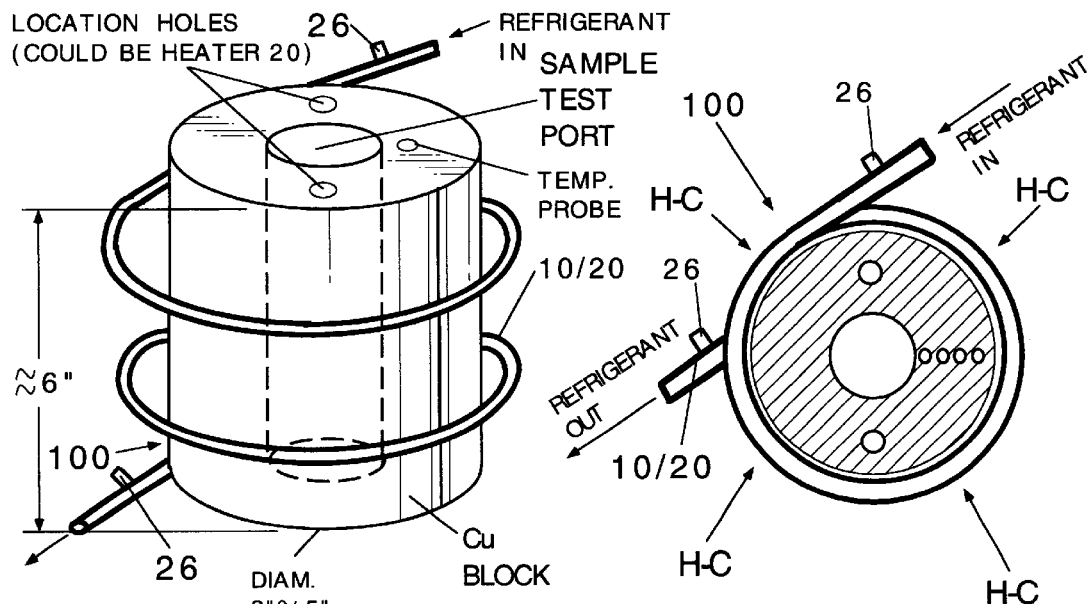
Fig. 6A
Fig. 6B
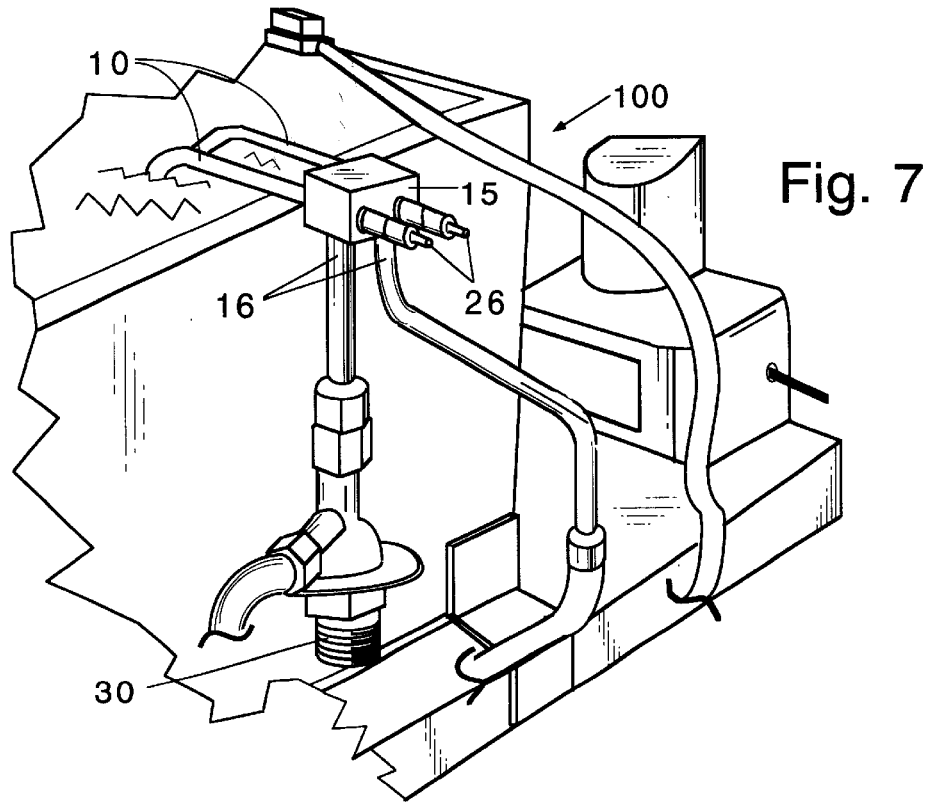
Fig. 7

US 6,755,044 B1

HEATER-EVAPORATOR

This claims benefit under 35 USC 119(e) of U.S. provisional patent application No. 60/353,337 filed on Feb. 1, 2002 A.D. The complete specification of that application is incorporated herein by reference.

FIELD AND PURVIEW

The present invention concerns a hollow refrigeration fluid evaporator body with which is incorporated a heater. For instance, the evaporator body may be a tube or a cavity in a block; and the heater may be of the electrical resistance type formed as a line extending through the tube or formed to reside in the cavity, or may be provided by the evaporator body itself.

BACKGROUND INFORMATION

Known analytical instrumentation for testing physical properties of liquids such as oils, transmission fluids, fuels, and paints can involve cooling of a test sample in a bath of air or liquid, for example, methanol or ethylene glycol, or in a solid block. Typical configurations include a refrigerant line to cool the bath or block and a heating element elsewhere in the bath or block. Thus, temperature control, to include under cooling conditions, can be carried out.

In other applications such as room climate control, heating and any cooling are carried out by separately located heating and cooling elements. In common refrigerators and walk-in coolers, it is typical for cooling to be provided by a system in which only cooling is provided for maintaining temperature.

Such systems, as useful and valuable as they are, are not without drawbacks. The need to provide separated cooling and heating elements can complicate or clutter a configuration. In systems in which space is at a premium, this can be a critical concern. Then, too, temperature control throughout a system having separated cooling and heating elements can be less than ideal.

It would be desirable to improve upon such systems. It would be desirable to ameliorate if not completely overcome such drawbacks.

BRIEF SUMMARY

The present invention provides a heater-evaporator, which comprises a hollow refrigerator fluid evaporator body with which is incorporated a heater. The invention is useful in refrigeration and temperature control.

Significantly, by the invention, the art is improved in kind, and drawbacks such as those mentioned previously are ameliorated if not completely overcome. In particular, elements are provided which function as refrigerant evaporators as well as heaters. Space can be used more efficiently, and temperature control can be brought to a higher level of perfection. Thus, temperature can be brought, for instance, to the desired level, and heating or cooling can maintain it in the process. The invention can be adapted for employment in air, liquid, and solid baths, and in a host of target applications, to include analytical instruments, for example, viscometers, rheology-testers, and dynamometers, other cold-bath testing devices, which can include for testing engine oils, gear oils, transmission and hydraulic fluids, fuels, paints, and so forth; and container and room air conditioning devices, and so forth. Also, the system can be employed as a line warmer or preheater for different applications. As well, the invention could be employed to provide protection for a refrigeration system by adding superheat to a system.

Numerous further advantages attend the invention.

DRAWINGS INDEX

The drawings form part of the specification hereof. With respect to the drawings, which are not necessarily drawn to scale and in which dimensions, in inches, may be provided, which may be considered to be approximate, the following is briefly noted:

FIG. 3 represents plan views of another heater-evaporator embodiment of the invention, which can be especially beneficially employed in a solid bath/block application. The views are as follows: exploded front perspective (A); top plan (B) without cap installed; and exploded, sectional side plan (C) taken along C—C from FIG. 3B.

FIG. 6 represents additional improvements with respect to a heater-evaporator of the invention, a solid block instrument. There are depicted top perspective (A) and top (B) views.

FIG. 7 represents an external view of a heater-evaporator embodiment of the present invention, which is part of a system that includes the heater-evaporator of FIG. 2 installed in a liquid bath, and which includes a constant pressure valve.

ILLUSTRATIVE DETAIL

The invention can be further understood by the present detail, which may be read in view of the drawings. Such is to be taken in an illustrative and not necessarily limiting sense.

In general, the heater-evaporator includes a hollow refrigeration fluid evaporator body with which is incorporated a heater. For instance, the evaporator body may be a tube or a cavity in a block, or be of any other suitable shape. Thus, for example, a block may be in the form of a cube or cylinder and have one cavity or more inside with one cavity having a plurality of compartments in communication with each other so that refrigerant may pass between or among them, or with the single cavity having no smaller compartments, or with the plurality of cavities in communication with one another, isolated from one another, or some in communication and some isolated. The tube may be in any suitable shape, to include straight wand, U-shaped wand, serpentine wand, coil and so forth. As may be appropriate, such can be configured in almost any form. The body may be of any suitable material that can contain refrigerant and conduct heat, and so, a metal or alloy of gold, copper, iron, and so forth may be employed. Copper and stainless steel are preferred. The heater may be of any suitable type such as the electrical resistance type, a hot liquid or gas in a tube or other line, which may be provided by a boiler or enclosed gas heater, by burning of fuel, by induction such as radiation activation of a radiation-sensitive material which gives off heat when a suitable radiation flux is sent through, for example, microwave radiation, and so forth. For instance, the heater may be formed as a line extending through the inside of the tube or formed to reside in the cavity, for an example, heated by electrical resistance, or provided by the evaporator body itself, say, heated by electrical resistance. The electrical resistance heater may be available commercially such as FIREROD heater (WatLow Inds., Hannibal, Mo.). An advantageous situation that may approach ideal is one in which the heating is provided by and on the outside of the evaporator body serving as the heater. Electrical resistance and induction may be employed together or in alternating sequence to heat a suitable heater. In the cavity or line formed from the hollow body, refrigerant can course to provide a means for cooling. The heater provides a means for heat. Beneficially, the combination of heating and cooling is provided in the same unit.

Figure 1A:
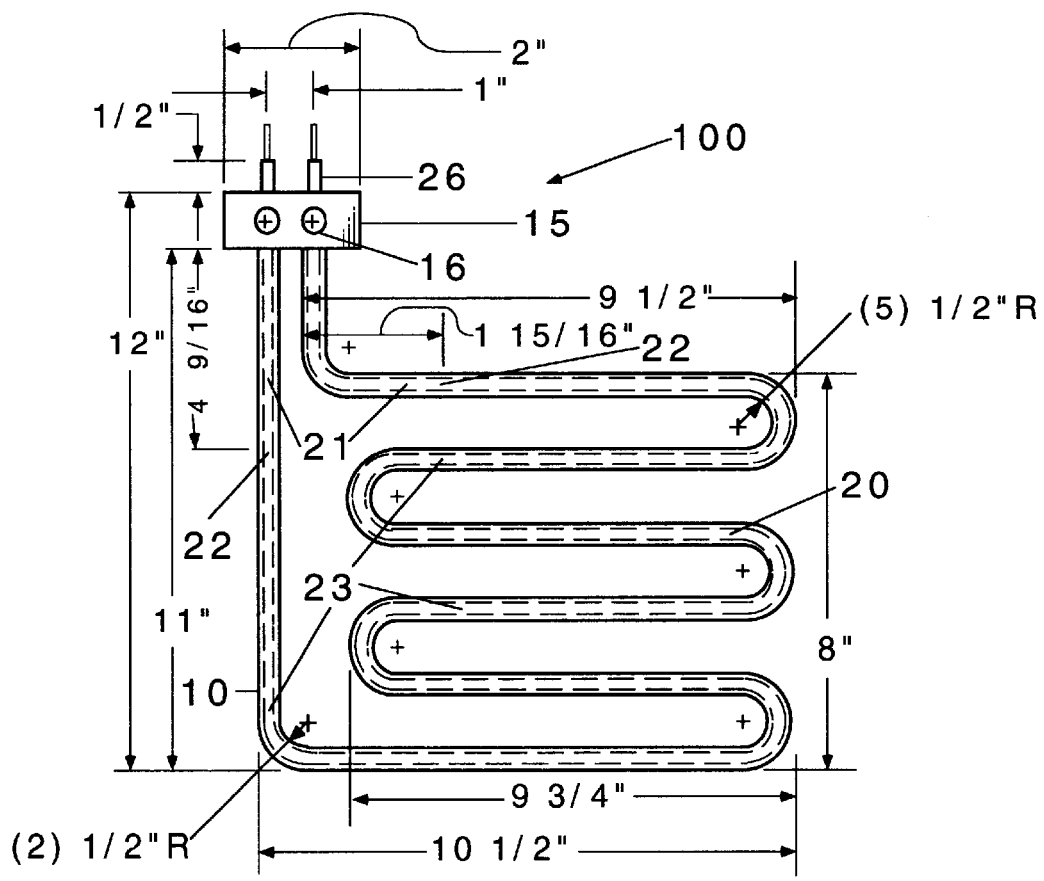
FIG. 1 represents plan views of a heater-evaporator embodiment of the invention, which can be especially beneficially employed in an air bath application. These views are top (A); side (B); and partial side detail (C) along arrow C of FIG. 1B.
Figure 1B:
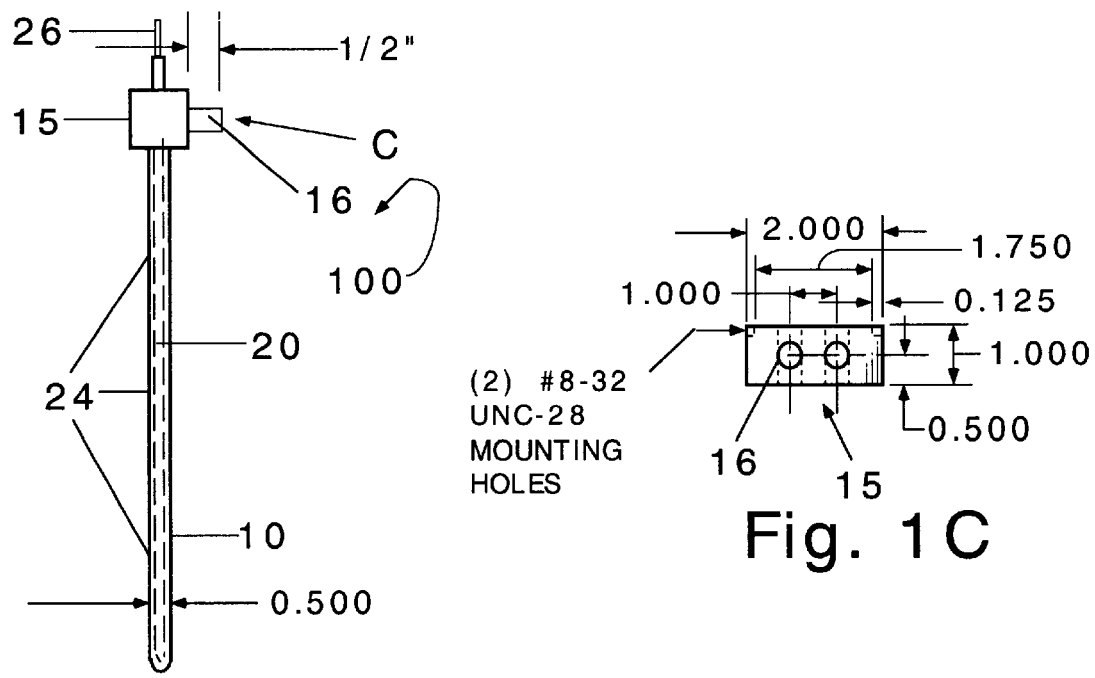
Figure 1C:
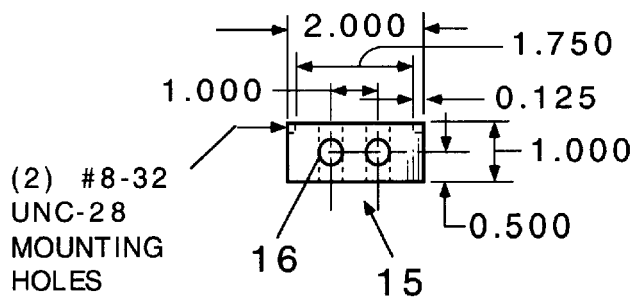
Figure 2A:
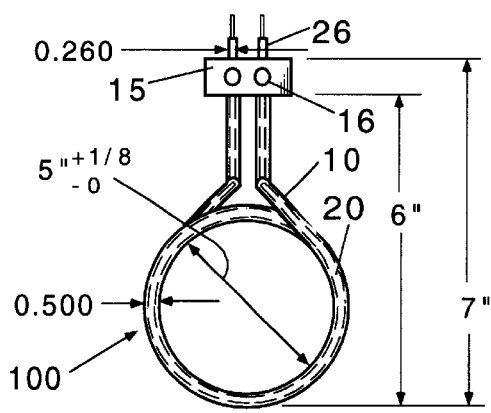
FIG. 2 represents plan views of another heater-evaporator embodiment of the invention, which can be especially beneficially employed in a liquid bath application. There are depicted bottom (A); rear (B); side (C); and detailed partial bottom (D) views.
Figure 2C:
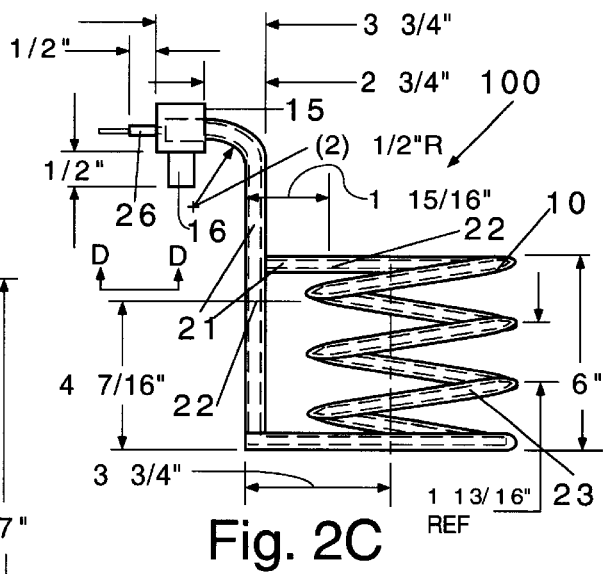
Figure 2B:
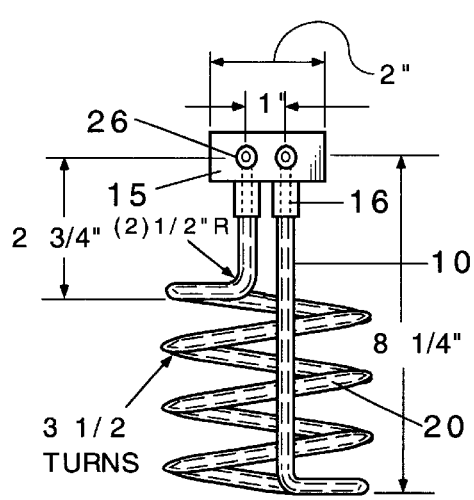
Figure 2D:
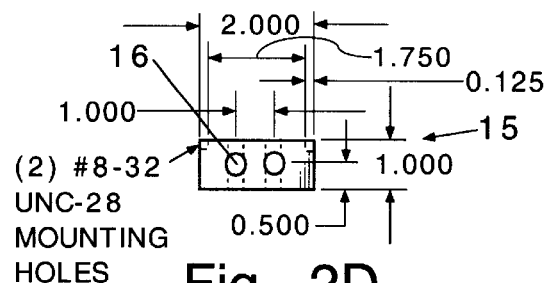
Figure 4A:
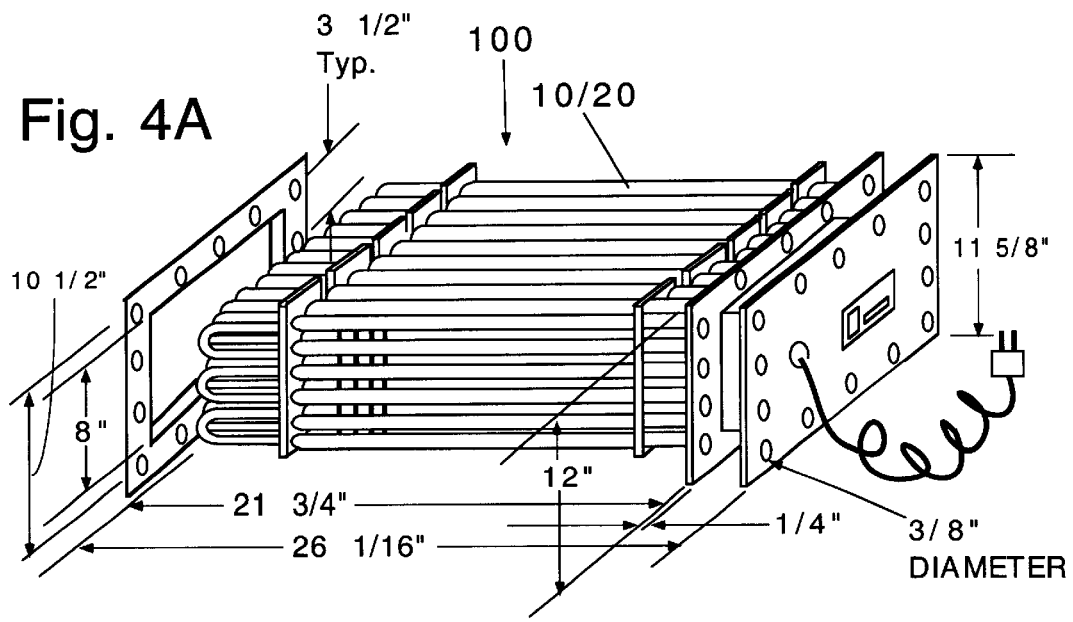
FIG. 4 represents a perspective view of another heater-evaporator embodiment of the invention in which the evaporator body also serves as the heater. The plan views depict an embodiment which can be especially beneficially employed as a modular duct heater-cooler (A); select heating by electrical resistance (B); and heating by induction (C).
Figure 4B:
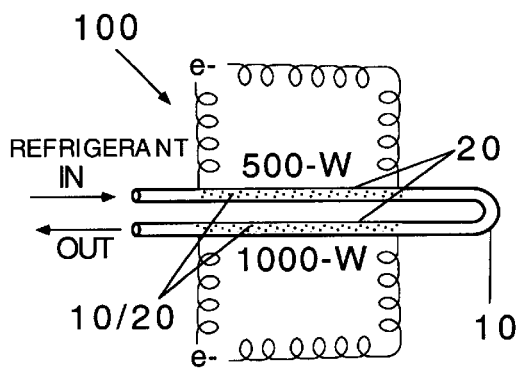
Figure 4C:
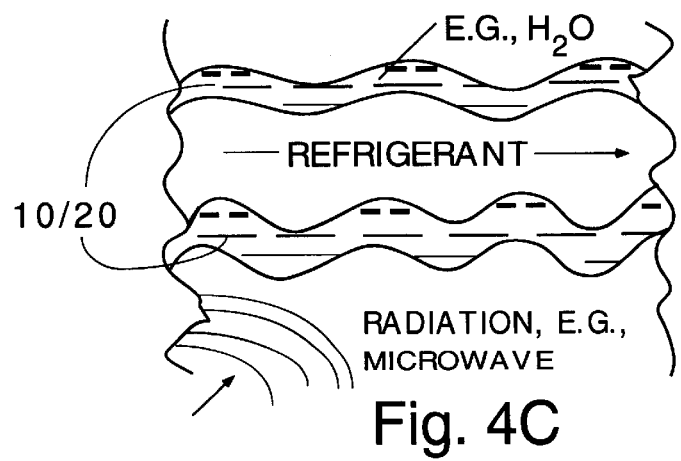
Figure 5A:
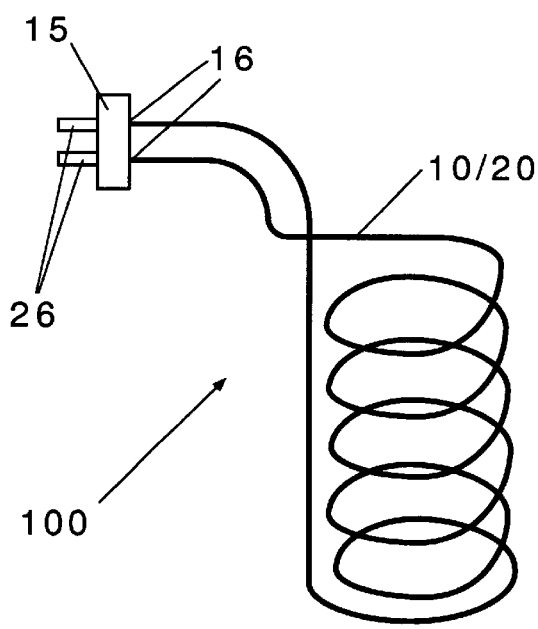
FIG. 5 represents additional improvements with respect to a heater-evaporator of the invention. The views are as follows: side plan of a coil (A); side plan of a coil with radiating fins (B); side plan of terminating parts (C); and sectional view (D) taken along D—D from FIG. 5C.
Figure 5B:
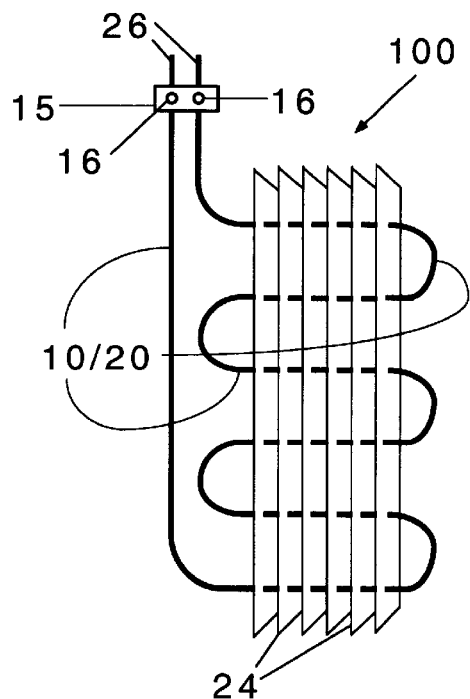
Figure 5C:
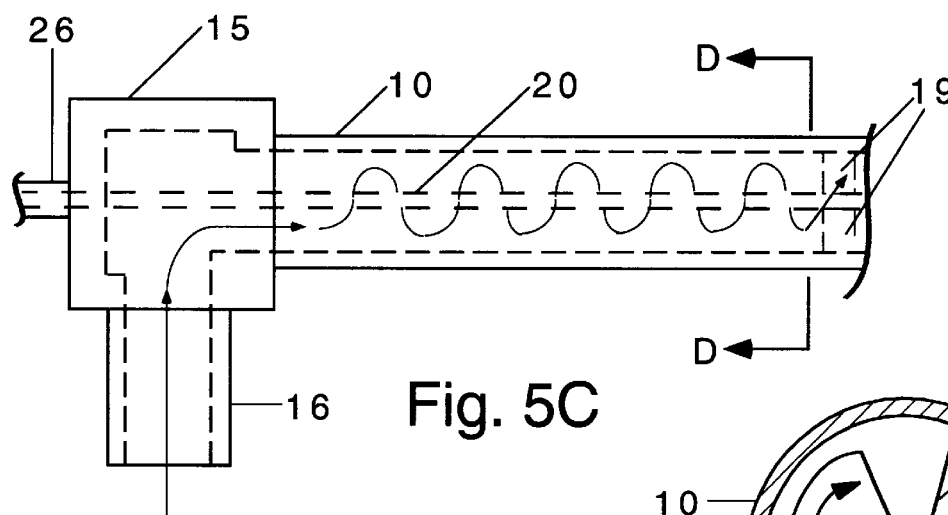
Figure 5D:
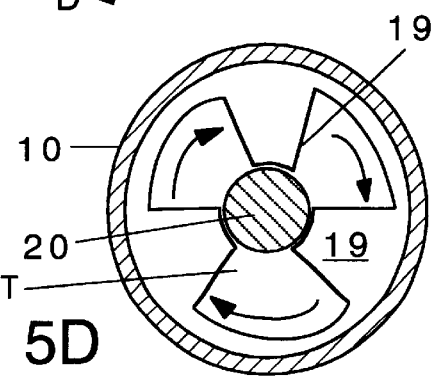
Figure 8:
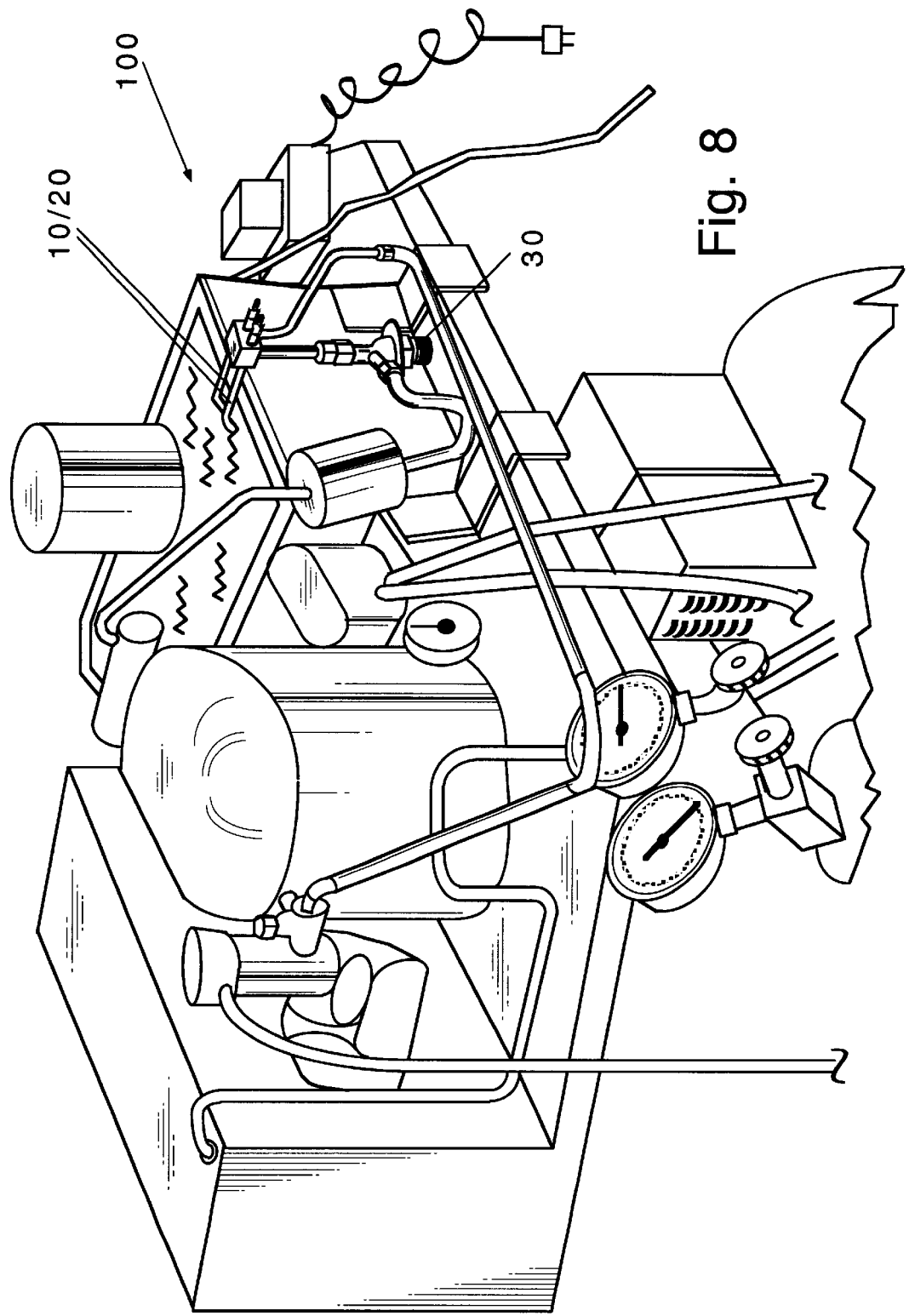
FIG. 8 represents an external view of a heater-evaporator system of the invention, part of which is in found FIG. 7, which includes accessories to include pumps and so forth.

With respect to the drawings, heater-evaporator 100 has hollow body 10 incorporated with heater 20. The body 10 can be in the form of a tube (FIGS. 1, 2, 4, 5), cavity (FIG. 3) with inner coolant-passage holes 11, and so forth. Termination block (FIGS. 1–3, 5, 7, 8) may have hollow, coolant-line connector stubs 16. Cap 17 may be required (FIG. 3). Bushing or shim 19 may space the body 10 apart from a separate internal heater 20 (FIG. 5). The heater 20 can be a conforming line type element heated by electrical resistance (FIGS. 1, 2, 5) that can extend through the inside of the tube 10, and may include a non-heating portion 21 bounded by hot/cold junction 22 (FIGS. 1, 2). Between the junctions 22 is heating portion 23. Radiation fins 24, say, of the same material as the body 10, may be attached, and can be especially beneficial in a configuration adapted for employment in an air bath. Termination studs 26 for the heater 20 may be provided. Such a heating element is, generally speaking, in direct contact with the refrigerant coursing through the body 10. The heater 20 may be a simple rod element, which is heated by electrical resistance (FIG. 3) that is inserted into a drilled or otherwise provided hole or well in a portion of the body 10, and it may not be in direct contact with refrigerant coursing through the tube hollow or cavity of the body 10. The heater 20 may be the same as the hollow body 10 (FIG. 4) such as where electrical resistance of a tube through which courses refrigerant is taken advantage of to provide heat when an electric current is passed, which may be on the outside in a limited portion of the body and in which different levels of resistance and so heat is supplied, or the same element serving as the body 10 and heater 20 may be heated by induction. Additional improvements may be provided (FIGS. 5, 6) including a solid block version of devices to test lubricants in a laboratory, however, now without a liquid cooling bath (FIG. 6) so that a liquid bath version of the otherwise same or similar device can be replaced. Constant pressure valve 30 may be employed (FIGS. 7, 8). Accessories to include pumps and so forth can be those known in the art (FIGS. 7, 8).

The following table provides further detail, the dimensions or values of which may be considered to be approximate, with the dimensions in inches, especially with respect to FIGS. 1–6:

TABLE

| FIG. | Comment |
|---|---|
| 1, 2 | Heater-evaporator specifications:<br><br>Heater rating: 110 volts, 1000 watts.<br>Element material: 0.260 diam., #316L stainless steel.<br>Termination: #6-32 threaded stud terminal 26 with two nuts, two washers, and ceramic insulator.<br>Element seal: Epoxy resin.<br>General tolerance: ±⅛-in. unless otherwise noted.<br>Element 20 assembled inside 0.500 × 0.035 wall #316L stainless steel tube 10.<br>Supplied with one 2-in. × 1-in. × 1-in., #304 stainless steel coolant fitting 15, welded to element sheath.<br>Two #304 stainless steel 0.437 O.D. × 0.375 I.D. stubs 16 welded to the fitting 15. |
| 1 | Further specifications:<br><br>Watt density: 19.22 watts per square inch.<br>Cold end length: 6¹⁄₁₆ inches.<br>Some instrumental applications in oil-testing apparatus:<br><br>Tannas PLUS-2 (smaller 2-head size) Scanning Brookfield Technique (SBT) viscometer cooling-liquid bath.<br>See, e.g., U.S. Pat. No. 5,503,002.<br>Tannas Foam Air Bath. See, e.g., U.S. Pat. No. 6,009,748.<br>Mini-Rotary Viscometer (MRV/TP1) block or bath.<br>Compare, U.S. Pat. No. 5,852,230 and<br>U.S. patent application Ser. No. 10/077,236.<br>Kinematic Viscosity (KV) bath. Note, U.S. patent application Ser. No. 60/354,994. |
| 2 | Further specifications:<br><br>Watt density: 17.41 watts per square inch.<br>Cold end length: 7⁷⁄₁₆ inches.<br>Some instrumental applications in oil-testing apparatus:<br><br>Tannas PLUS-4, PLUS-8 (4-, 8-head sizes) SBT viscometer cooling-liquid baths. See again, the '002 patent.<br>MRV/TP1 block or bath.<br>Cold Cranking Simulator (CCS). Note, U.S. Pat. No. 3,350,922. |
| 3 | Heater-evaporator specifications:<br><br>The body 10 can be copper, stainless steel, etc.<br>Volume of the cavity of the body 10 should be equivalent to a 5-foot, ⅜-inch diameter tube.<br>Four inner coolant-passage holes 11 are present, one through each of the four inner chamber walls, so as to allow vapor passage and flow among the open volume of the subchambers.<br>Refrigerant line connector stubs 16, both inlet and outlet, can be ⅜-in. diam., soldered to communicate with orifices that form tubes in the block 15 for inlet and outlet of refrigerant in the cavity volume of the block 10, where, inside, both inlet and outlet tubes open to the chamber cavity from the bottom.<br>Cap 17 is to be silver-brazed to the body 10 to seal.<br>Heater rating: 110-volt AC, 600 watts.<br>Electrical elements 26 may be located in any suitable spot such as on the sides rather than the bottom.<br>Temperature range: −40° C. to +80° C.<br>Some instrumental applications in oil-testing apparatus:<br><br>Tannas PLUS-4, PLUS-8 (4-, 8-head sizes) SBT viscometer cooling-liquid baths.<br>MRV/TP1 block or bath.<br>Cloud and pour test bath.<br>CCS. |
| 4 | Evaporator body 10 generally also serves as heater 20:<br><br>A. Duct insert can be modified to be heater-cooler 100. Dimensions are typical; lateral dimensions may vary.<br>B. Heating can be by electrical resistance selected from |

TABLE-continued

| FIG. | Comment |
|---|---|
|  | between two separate areas of the body/heater 10/20 which can have the same or different heat outputs, say, one 500-W, the other 1000-W, or select both.<br>C. Heating can be by radiation activation of the body 10 material or another material, say, water, in the body 10, which may be of glass, to provide the heater 20. |
| 5 | Heater-evaporator specifications:<br><br>Coils can be configured in almost any shape considering the minimum bend radius for the outer tubing 10.<br>Run refrigerant through outer tube 10, say, of ½-in. to ⅝-in. diameter, in which may be internal heater 20, say, of 3/16-in. to ¼-in. diameter.<br>Goal: No direct contact between tube 10 and heater 20.<br>Non-electrically and/or thermally conducting bushings 19 may space separate the internal heater 20 apart from tube 10, helping to avoid electrical shock and/or hot spots.<br>Heater rating: 110 or 220 volts, 1000–1200 watts.<br>Could be low voltage (E), high amperage (I) such as E = 0.3, I = 300. |
| 6 | Solid block SBT:<br><br>Coil evaporator 10 surrounds copper test block to send "cold" flux toward sample.<br>Coil 10 and/or test block includes heater 20 to control "hot-cold" flux (H-C) or temperature in test block.<br>One heated block and coil per sample test port.<br>Separate activation of each heated block and/or coil.<br>Can be fit to other system otherwise using methanol bath. |

In the practice of the invention, both air and liquid baths can be controlled to 0.1 degree C. Solid block devices can be controlled analogously. Slugging liquid refrigerant can be avoided as well, for instance, by replacing a section of an existing line with a heated section, so that, when the proper amount of heat is applied, gas, not liquid, is drawn into the pump. Accordingly, efficiency can be increased so that, whereas a standard refrigerant system operates at an about 20-degree F. (ca. 9-degree C.) superheat value, with the pinpoint control made available hereby, the thus-modified system may be practically operated at an about 3-degree F. (ca. 1-degree C.) superheat-value. Cooling can be from below ambient temperature, which may be a temperature the same as or different from, say, above, standard room temperature, to about –70 degrees or –80 degrees C., or even lower, and points in between. In addition to or in amplification of the foregoing uses, the invention can be employed in a house trailer, where space is at a premium, or in any application with respect to air, to include electric forced air furnaces in which the evaporator can cool air to temper the heat or serve as an air conditioner; as a refrigeration system; as a regulator of fuel temperature in vehicles, to include racing cars; as a regulator of soils and hydroponic solutions in greenhouses and stadiums; in a hydronic water heating system employing gas heat, where an evaporator in the system can cool the water, thus tempering its temperature; as a range top element, which can both heat and cool; and in many other applications, to include in the laboratory setting where heating and/or cooling is desired. In a case such as the latter case, a standard heater or cooler in one portion of a bath may be run against a heater-evaporator of the invention in another portion of the bath. Thus, an opposed temperature bath could be employed as may be desired in certain testing. Liquid samples may comprise the test sample. The liquid may be, for instance, a fuel or an oleaginous liquid, for example, jet fuel A, kerosene, diesel oil, motor oil, gear oil, automatic transmission fluid, and so forth and the like.

The useful lifetime of the heater-evaporator can be quite extensive. In particular, presuming that a heating element is a limiting factor in the life of the heater-evaporator, its life can be a long time due to being cooled by the refrigerant.

Conclusion

The present invention is thus provided. Various features, parts, subcombinations and combinations can be employed with or without reference to other features, parts, subcombinations or combinations in the practice of the invention, and numerous adaptations and modifications can be effected within its spirit, the literal claim scope of which is particularly pointed out as follows:

I claim:

1. A heater-evaporator comprising a hollow, enclosed refrigeration fluid evaporator body, which is made of a suitable material that can conduct heat, and through and inside which body a passage is thereby provided that can contain refrigeration fluid that can course and evaporate, afterwards to be condensed outside said passage for return thereto, in a continuous cycle to provide refrigeration for a system outside the passage, and with which body is incorporated a heater, wherein the heater is heated by induction.

2. The heater-evaporator of claim 1, which is employed in conjunction with a laboratory test device requiring refrigeration of a test sample and temperature control.

3. The heater-evaporator of claim 2, wherein the laboratory test device is for testing fluid properties of the test sample.

4. The heater-evaporator of claim 1, wherein the body encloses the heater, which is separate from but inside said body.

5. The heater-evaporator of claim 1, wherein the heater is provided by said body itself.

6. The heater-evaporator of claim 5, wherein the induction is by microwave radiation.

7. In a laboratory test device requiring refrigeration and temperature control, the improvement which comprises employing a heater-evaporator including a hollow, enclosed refrigeration fluid evaporator body, which is made of a suitable material that can conduct heat, and through and inside which body a passage is thereby provided that can contain refrigeration fluid that can course and evaporate, afterwards to be condensed outside said passage for return thereto, in a continuous cycle to provide refrigeration for a system outside the passage, and with which body is incorporated a heater.

8. The device of claim 7, wherein said body and passage form a tube.

9. The device of claim 8, wherein said tube surrounds a thermally conductive block that contains at least one sample port.

10. The device of claim 8, wherein said tube is immersed in a liquid bath for control of temperature of a test sample that is also immersed in the liquid bath.

11. The device of claim 7, wherein said passage is in a form of a cavity that is not a tube.

12. The device of claim 7, which tests liquid samples.

13. The device of claim 12, which is part of a viscometer.

14. The device of claim 7, in which slugging of liquid refrigerant is avoided; and which provides for at least one of the following:
  control of temperature to 0.1 degree C.; and an about 3-degree F. superheat value during operation.

15. The device of claim 10, wherein the tube includes a form of a generally helical ring.

16. The device of claim 13, wherein said body and passage form a tube, and the tube is immersed in a liquid bath for control of temperature of a test sample that is also immersed in the liquid bath.

17. The device of claim 13, wherein direct refrigeration of a test block, without cooling of an intermediate liquid, is present.

18. A method of cooling and controlling temperature, which comprises:

providing a heater-evaporator including a hollow, enclosed refrigeration fluid evaporator body, which is made of a suitable material that can conduct heat, and through and inside which body a passage is thereby provided that can contain refrigeration fluid that can course and evaporate, afterwards to be condensed outside said passage for return thereto, in a continuous cycle to provide refrigeration for a system outside the passage, and with which body is incorporated a heater;

providing refrigeration for the system outside the passage by causing the refrigeration fluid to course and evaporate through and inside said passage, afterwards to be condensed outside said passage for return thereto, in a continuous cycle; and activating the heater while the refrigeration fluid courses and evaporates inside said passage.

19. The method of claim 18, in which slugging of liquid refrigerant is avoided; and which provides for at least one of the following:

control of temperature to 0.1 degree C.; and an about 3-degree F. superheat value during operation.

20. The method of claim 18, wherein said system is part of a viscometer.

* * * * *